(12) United States Patent
Wu

(10) Patent No.: US 9,289,125 B2
(45) Date of Patent: Mar. 22, 2016

(54) VISION PROTECTION METHOD AND SYSTEM THEREOF

(71) Applicant: Roger Li-Chung Wu, West Covina, CA (US)

(72) Inventor: Roger Li-Chung Wu, West Covina, CA (US)

( * ) Notice: Subject to any disclaimer, the term of this patent is extended or adjusted under 35 U.S.C. 154(b) by 0 days.

(21) Appl. No.: 14/532,016

(22) Filed: Nov. 4, 2014

(65) Prior Publication Data

US 2015/0055087 A1 Feb. 26, 2015

Related U.S. Application Data

(63) Continuation of application No. 14/300,206, filed on Jun. 9, 2014, which is a continuation-in-part of (Continued)

(51) Int. Cl.

| | |
|---|---|
| *A61B 3/00* | (2006.01) |
| *A61B 3/14* | (2006.01) |
| *A61B 3/18* | (2006.01) |
| *G06F 3/01* | (2006.01) |
| *G06K 9/00* | (2006.01) |
| *G06Q 10/10* | (2012.01) |
| *A61B 3/11* | (2006.01) |
| *A61B 3/113* | (2006.01) |
| *A61B 3/12* | (2006.01) |

(Continued)

(52) U.S. Cl.

CPC . *A61B 3/18* (2013.01); *A61B 3/112* (2013.01); *A61B 3/113* (2013.01); *A61B 3/12* (2013.01); *A61B 3/14* (2013.01); *A61B 5/1075* (2013.01); *A61B 5/1103* (2013.01); *A61B 5/1116* (2013.01); *A61B 5/1128* (2013.01); *A61B 5/486* (2013.01); *A61B 5/489* (2013.01); *A61H 5/00* (2013.01); *A61M 21/02* (2013.01); *G06F 3/013* (2013.01); *G06K 9/00597* (2013.01); *G06Q 10/109* (2013.01); *G09G 5/00* (2013.01); *A61B 5/1176* (2013.01); *A61B 2503/20* (2013.01); *A61B 2560/0266* (2013.01); *A61B 2560/0271* (2013.01); *A61H 2201/5007* (2013.01); *A61H 2201/5043* (2013.01); *A61H 2201/5064* (2013.01); *A61H 2201/5092* (2013.01); *A61M 2021/005* (2013.01); *A61M 2021/0027* (2013.01); *A61M 2205/056* (2013.01); *A61M 2205/3303* (2013.01); *A61M 2230/62* (2013.01); *A63F 2300/8094* (2013.01); *G06F 2203/011* (2013.01); *G09G 2354/00* (2013.01); *G09G 2356/00* (2013.01); *G09G 2360/144* (2013.01); *G09G 2360/145* (2013.01)

(58) Field of Classification Search

USPC .................................. 351/203, 206, 209, 246

See application file for complete search history.

(56) References Cited

U.S. PATENT DOCUMENTS 8,884,735 B2 * 11/2014 Li-Chung ............ G06Q 10/109
340/3.1

*Primary Examiner* — Jack Dinh

(74) *Attorney, Agent, or Firm* — Raymond Y. Chan; David and Raymond Patent Firm

(57) ABSTRACT

The vision protection method and system thereof is provided to ensure a viewer to rest his/her eyes after viewing on an electronic device for a certain period, wherein the eyesight protection method includes the steps of detecting one of more working parameters of the viewer in responsive to a preset working threshold in a working mode of the electronic device during the viewer is working on a current work displaying by the electronic device; switching the working mode of the electronic device to a resting mode; and switching the electronic device from the resting mode back to the working mode to resume the display of the current work of the electronic device. Therefore, the viewer is enforced to rest his/her eyes after every certain period.

20 Claims, 4 Drawing Sheets

Related U.S. Application Data application No. 13/135,995, filed on Jul. 19, 2011, now Pat. No. 8,884,735, which is a continuation-in-part of application No. 12/313,235, filed on Nov. 17, 2008, now Pat. No. 8,884,734, application No. 14/532,016, which is a continuation of application No. 14/289,634, filed on May 28, 2014, now Pat. No. 9,165,263, which is a continuation of application No. 12/313,235, filed on Nov. 17, 2008, now Pat. No. 8,884,734.

(51) Int. Cl.

| | | |
|---|---|---|
| *A61B 5/11* | (2006.01) |
| *A61B 5/00* | (2006.01) |
| *A61H 5/00* | (2006.01) |
| *A61M 21/02* | (2006.01) |
| *A61B 5/107* | (2006.01) |
| *G09G 5/00* | (2006.01) |
| *A61M 21/00* | (2006.01) |
| *A61B 5/117* | (2006.01) |

VISION PROTECTION METHOD AND SYSTEM THEREOF

CROSS REFERENCE OF RELATED APPLICATION

This is a Continuation application that claims the benefit of priority under 35U.S.C.§119 to a non-provisional application, application Ser. No. 14/300,206, filed Jun. 9, 2014, which is a Continuation-In-Part application that claims the benefit of priority under 35U.S.C.§119 to a non-provisional application, application Ser. No. 13/135,995, filed Jul. 19, 2011, which is a Continuation-In-Part application of a non-provisional application, application Ser. No. 12/313,235, filed Nov. 17, 2008.

This is also a Continuation application that claims the benefit of priority under 35U.S.C.§119 to a non-provisional application, application Ser. No. 14/289,634, filed May 28, 2014, which is a Continuation application that claims the benefit of priority under 35U.S.C.§119 to a non-provisional application, application Ser. No. 12/313,235, filed Nov. 17, 2008.

BACKGROUND OF THE PRESENT INVENTION

1. Field of Invention

The present invention relates to a method for limiting the viewing time of a viewer to protect the viewer's eyesight, and more particularly to a method of controlling an electronic device display for ensuring the viewers to rest their eyes after each predetermined period of time.

2. Description of Related Arts

Electronic devices are indispensable for our daily lives. People use computers for work, play video games and watch TVs during their leisure time and etc. Since many people spend a vast portion of their daily lives fixating on display screens of electronic devices, to protect a viewer's eyesight from excessive usage of any electronic device and prevent eye straining become a dramatic issue nowadays.

One of the most important factors in protection of the eyesight for electronic device viewers is to have an intermittent rest for their eyes follow a certain time of use. To protect the eyes from being over-used, the viewer should take a rest and/or do some eye exercises to help relax the muscles of the eyeballs. For example, children spend much time focusing on watching the displays of the electronic devices, such as computers for playing the ever-increasing number of games available. To compensate, the eyeball is thought to grow longer, so less effort is needed to focus up close on the computer display. When this happens, the elongated eye can no longer focus on distant objects. After the muscle of the eyeball being elongated too long, the muscle will loose its flexibility for adjusting the focus on distant objects, so that the eyesight problems such as nearsightedness and eye straining can occurred.

Even though people know how important it is to relax the eyeball muscles timely, people tend to forget taking a break and resting their eyes after viewing the display for a certain time. When people put themselves in work or indulge in a video game, it is hard to interrupt the work or video game to rest their eyes. An enforcing feature is needed to remind the viewers not to overuse their precious eyes. It is crucial that this enforcing feature can interrupt the viewer's current work, such as playing video games on an electronic game device, editing files on computer, or watching TV, so that the viewer won't continue to strain his or her eyes from using these devices.

A working distance between the viewer and the display of the electronic device is another important factor. Keeping certain working distance can also help to prevent the eyesight problems from getting worse quickly as well. A method or system for detecting the working distance has a great need for protecting the eyesight. Moreover, younger kids, especially those with family history of nearsightedness, tend to be more likely to develop these visual problems at an earlier age. It is becoming increasingly difficult for their parents to monitor their usage pattern on these electronic devices. Therefore, a dedicated feature on these electronic devices that can monitor both the viewers' usage and working distance is indeed necessary and crucial if we want to slow down the development of visual problems for all users.

SUMMARY OF THE PRESENT INVENTION

An object of the present invention is to provide a vision protection method and system thereof for protecting electronic device viewers from excessive usage of electronic devices and preventing eye straining.

Another object of the present invention is to provide a vision protection method and system thereof for an electronic device viewer, so that the viewer will be forced to rest his/her eyes after a certain time of usage to protect the eyes from being over-used.

Another object of the present invention is to provide a vision protection method and system thereof for protecting an electronic device viewer by ensuring the viewers to have intermittent rests of their eyes for a certain time following a predetermined period of use for the electronic device display.

Another object of the present invention is to provide a vision protection method and system thereof for electronic device viewer for an electronic device viewer, wherein the electronic device is switched from a present working mode to another temporary resting mode for a certain resting time so as to stop the viewers from viewing the display that they are working on after each predetermined time period. In which, the resting mode remains activated until the predetermined resting time is over, and that after the predetermined resting period is over, the system resumes the operation of the working mode of the electronic device that the viewer was working on previously.

Another object of the present invention is to provide a vision protection method and system thereof for electronic device viewer, wherein the display of the working mode of the electronic device that the viewer is working on is preset to be temporarily blanked out as the screen freezes or is replaced by special graphics of the resting mode.

Another object of the present invention is to provide a vision protection method and system thereof for electronic device viewer, wherein the screen displayed during the resting mode of the system is adapted for protecting the eyesight with a pattern or a photo that is soothing for the eyes.

Another object of the present invention is to provide a vision protection method and system thereof for electronic device viewer, wherein the display of the resting mode of the system can be vision therapy exercises, programs, or games designed to relax the muscles of the eyeball.

Another object of the present invention is to provide a vision protection method and system thereof for electronic device viewer, wherein the display of the resting mode of the system for protecting the eyesight is an instruction for stretching exercise, so that the viewers not only get to rest their eyes but also relax the muscles of the neck, back, arms, and wrists during these enforced break times.

Another object of the present invention is to provide a vision protection method and system thereof for electronic device viewer, wherein the system will save all information that the viewer is working on before the system switches to the resting mode to ensure that no information, files or data are lost when the working mode resumes.

Another object of the present invention is to provide a vision protection method and system thereof for electronic device viewer, which includes a setting function where the user can customize the electronic device to set up the desired working time and resting time, wherein the setting function further has a function for inputting individual information such as age, so that the resting screen of the electronic device can display the simple games or eye exercises that is suitable for each age group.

Another object of the present invention is to provide a vision protection method and system thereof, wherein a distance detector is equipped to determine the appropriate working distance between the viewer and the electronic device display. The distance detector is used in conjunction with the system to ensure that a proper distance is kept between the viewer and the display of the electronic device. And in an event that such distance is violated, a warning message will appear on the screen of the electronic device, and if the message continues to be ignored for a predetermined period of time, the electronic device will automatically switch to the resting mode.

Accordingly, in order to accomplish the above objects, the present invention provides a method for protecting the eyesight of the electronic device viewer, comprising the following steps:

initiating a time counter when a viewer starts operating an electronic device, switching the electronic device from a current working mode to a resting mode after a predetermined working time expires to force the viewer from focusing at the display of the electronic device, and switching the electronic device from the resting mode back to the working mode after a predetermined resting time expires, enabling the viewer to resume his/her previous work, wherein a loop is formed for ensuring the viewer to rest his/her eyes by providing intermittent breaks. The loop is broken only when the electronic device is shut down.

In addition, the system of the present invention is equipped with a distance detector which is a device designed to detect a working distance between the monitor and the viewer, wherein a warning message appears on the screen of the electronic device if the working distance falls below a threshold. If the viewer continues to ignore the warning message for more than a predetermined time, the system will "freeze" the electronic device immediately for another predetermined period of time before it can resume operation.

These and other objectives, features, and advantages of the present invention will become apparent from the following detailed description, the accompanying drawings, and the appended claims.

DETAILED DESCRIPTION OF THE PREFERRED EMBODIMENT

Figure 1:
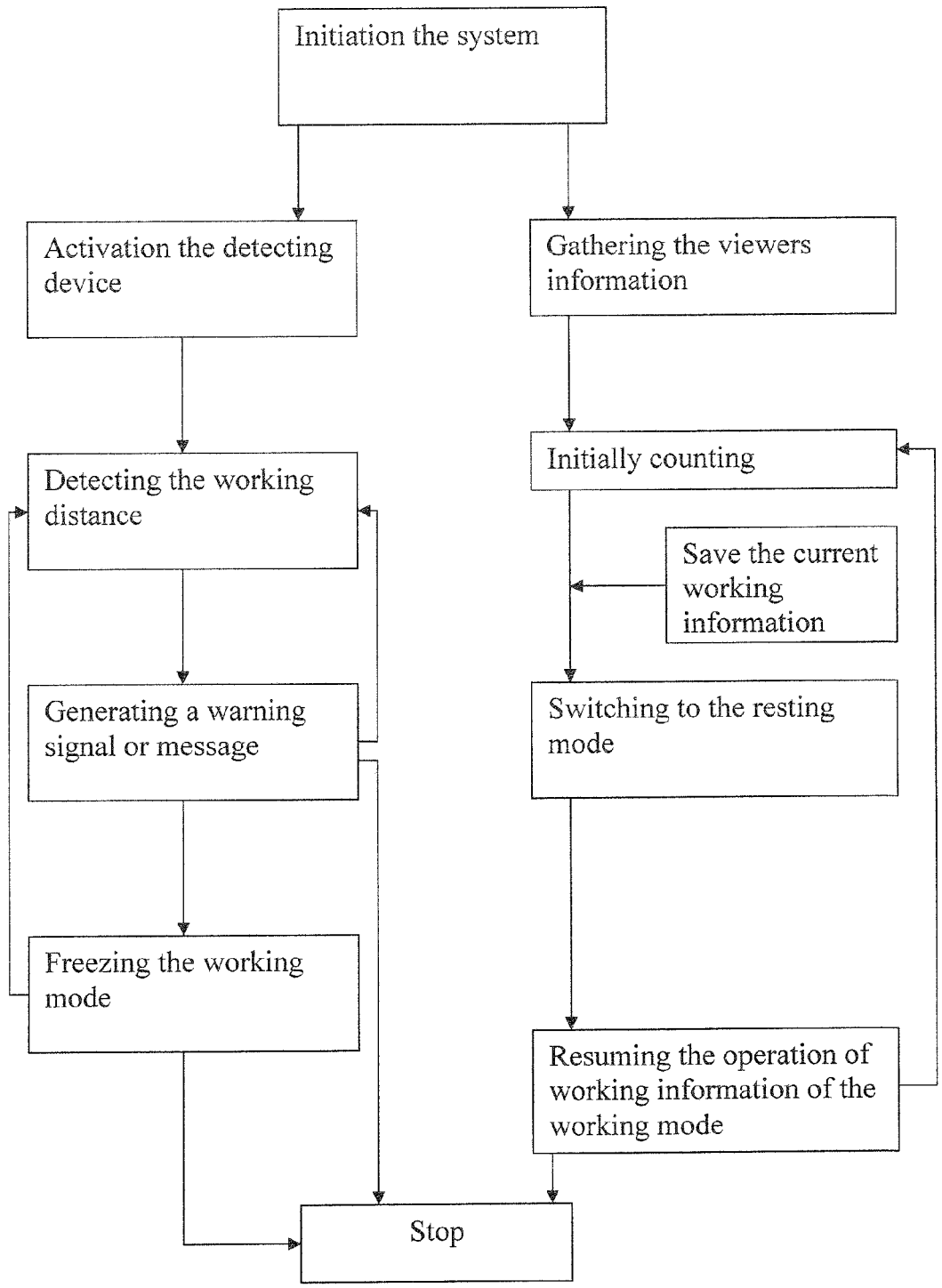
FIG. 1 is a flow chart of a method for protecting the eyesight of an electronic device viewer according to a preferred embodiment of the present invention.

Referring to FIG. 1 of the drawing, a flow chart of a method for eyesight protection of an electronic device viewer is illustrated, wherein the method includes a system comprising the following steps:

(a) initially counting down a predetermined working time in a working mode of the electronic device;

(b) switching the working mode of the electronic device to a resting mode after the predetermined working time expires for a predetermined resting time;

(c) resuming the operation of the electronic device from the resting mode back to the working mode after the predetermined resting time has elapsed; and (d) repeating the above step (a) to (c) to form a loop continuously until the viewer shuts down or halts operating the electronic device so as to ensure the viewer opportunities to rest his or her eyes after a certain period of usage.

The predetermined working time is a period of use time allowed on the electronic devices, for example, including but not limited to watching television, editing files on computer, playing video games or the likes, and the predetermined resting time is a period of time allotted for the resting mode. For example, the predetermined period of working and resting time are pre-set in the electronic device to one hour and ten minute respectively, so that after one hour of working on the electronic device, the electronic device will automatically switch from the working mode to the resting mode for ten minute.

In other words, the current work, such as editing files, playing games, watching television, with the electronic device will be idled by the resting mode to ensure the viewers to rest their eyes during the ten minutes resting time. The working mode of the electronic device will resume after the ten-minute resting mode expires. The system will then re-start another one-hour countdown (the predetermined working time), and the viewer will take another ten-minute rest after that one-hour countdown expires.

The electronic device can be a computer, a cellular phone, a PDA, a notebook computer, a hand-held gaming device, a television, a TV gaming device, and etc. When the electronic device is a programmable device such as a computer, the vision protection method of the present invention can be embodied as software, which can be purchased at a retail store or downloaded from the internet, being programmed in the electronic device to execute the above and following steps according to the present invention. The user/viewer can install it onto the electronic device with a few simple steps. The viewers can also register their names on the official website thereof and activate it by choosing the remote monitoring function on its website page without downloading or installing it to the electronic device if the viewers routinely use a public electronic device as long as that particular device has the Internet connection.

A good example of this will be computers at a public library. If a person routinely goes to a library and uses the computers there on a regular basis, he or she can still protect his/her eyesight by using this unique feature of the present invention, as long as that particular computer has an Internet connection, and the viewer does not close the window that has the eyesight/vision protection web page on. The eyesight/vision protection steps can cease running if the computer is turned off, the window with the web page is closed rather than minimized, or simply by clicking on a button on its website or pressing two or more designated keys simultaneously on the keyboard.

According to the preferred embodiment of the present invention, the resting mode is provided to temporarily freeze the current working mode for the period of resting time preset and ranged between 5 to 15 minutes after the predetermined working time. After the predetermined resting time is over, the electronic device resumes from the resting mode back to the working mode so the viewers can continue doing their previous work. Accordingly, the viewers of the electronic device are ensured to have intermittent rests of their eyes for a certain time following a predetermined period of time of use of the electronic device.

During the predetermined resting time of the resting mode, the electronic device is preset or programmed to temporarily freeze the current working mode, for example temporarily blanking out the screen display of the electronic device, so as to stop the viewers from viewing the display of the electronic device that they are working on after each predetermined working time.

According to the preferred embodiment of the present invention, during the resting mode, the screen display of the electronic device may also replace the working screen with a special graphic pattern or a photo that is soothing for the eyes during the predetermined resting time for protecting the eyesight of the viewer. Alternatively, during the predetermined resting time of the rest mode, the electronic device may play relaxing music, display soothing photos, or run special programs such as some simple visual therapy games for relaxing the muscles of the eyeball.

The resting mode can also "freeze" the current work on the electronic device by "freeze-framing" on the current work, displaying a plurality soothing pictures that are relaxing for the eyes, some simple games for eye movement exercises, or an instruction for stretching exercises, so as to force the viewers to rest their eyes. In other words, the resting mode is designed to interrupt the current work of the viewer while the viewer is using the electronic device for the predetermined working time. The resting mode serves as a forceful reminder for the viewers to rest their eyes and even provides some entertaining activities or visually enhancing exercises for the viewers while they wait for the "resting time" to expire when using the electronic device.

Before switching from the working mode to the resting mode, the electronic device is programmed to automatically save the current files, data, or working information accumulated by the viewer during the working mode, so that after the resting time is expired, the electronic device resumes normal operation and the viewers can continue from where they were left off right before the resting mode was activated. With this critical feature intact, the viewers can continue their previous work after taking a short break.

The present invention further includes a step of gathering the personal information of the user (viewer) to further customize this method and system of the present invention, where during the initial set-up, the viewers or the parents of the minor viewers can enter the viewer's names, age, and select their preference, usage settings such as the desired working time and the desired resting time according to the viewer's need. It also stores multiple sets of personal information so that it can accommodate multiple viewers for the same electronic device. The viewer can also select from a list of display options during the resting mode, such as a "freeze frame" display, pictures, games, instruction for visual relaxation or instruction for stretching exercise. The age information entered during the initial set-up will be used so that during the resting mode, the method and system of the present invention will choose the appropriate games or instructions suitable for that age group.

The vision protection method of the present invention further comprises a bypassing feature with a preset password that can be entered by people such as parents for emergency reasons. For example, if it is getting really late, and the viewer's work absolutely has to be done, the resting mode can be deactivated immediately by entering the password.

Figure 2:
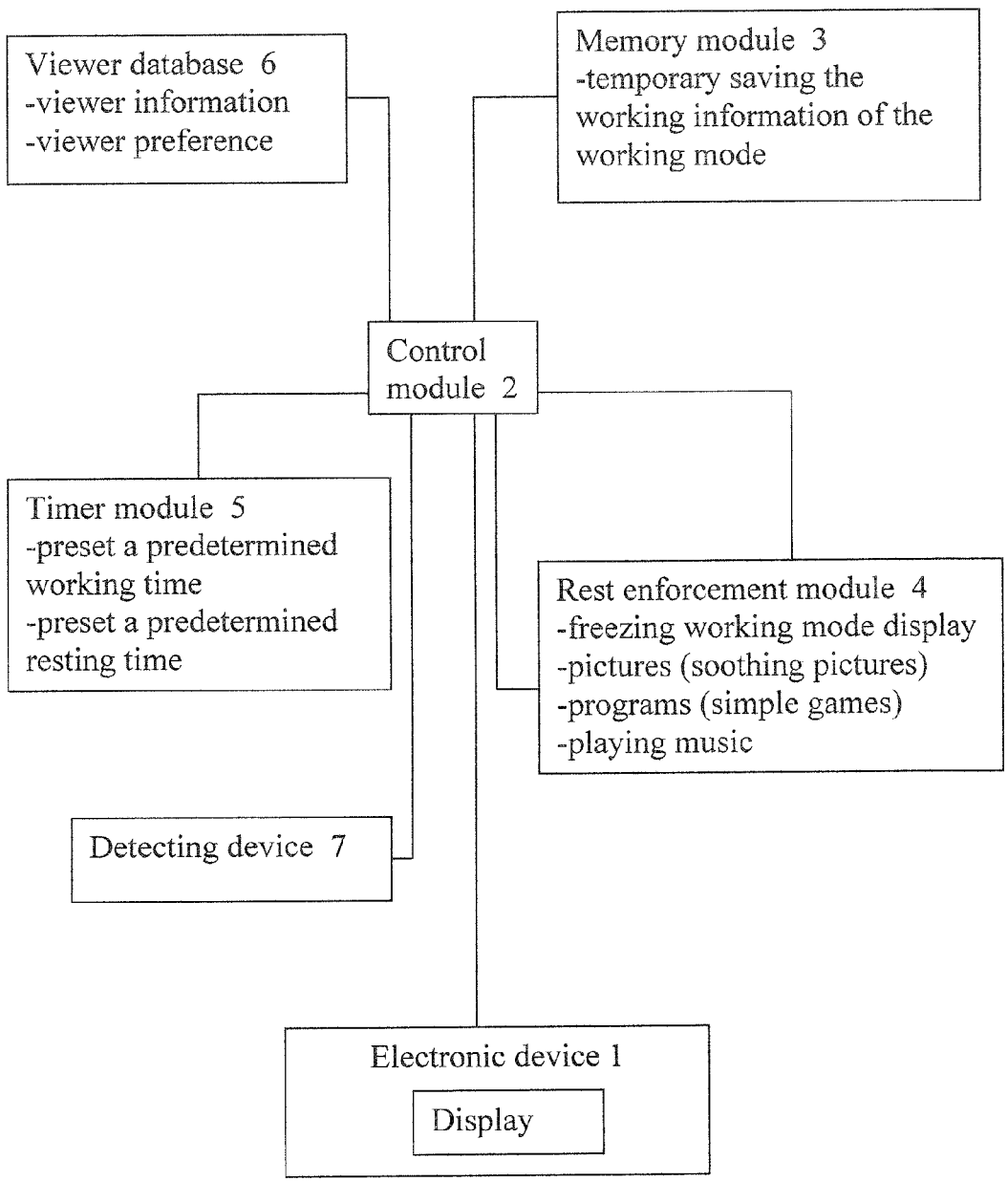
FIG. 2 is a block diagram of a vision protection system according to the preferred embodiment of the present invention.

The vision protection method of the present invention can be embodied to be performed by a system equipped with the electronic device 1 as shown in FIG. 2 of the drawings. The vision protection system for the viewer of the electronic device 1 comprises a control module 2 for coordinating the devices or modules, a memory module 3 for saving the working information, data, or files that the viewer is currently working on, a rest mode enforcement module 4 where a plurality of resting mode activities are stored, a timer module 5 that does the countdown for both the predetermined working time and resting time, and a viewer database 6 for saving the information and preference of the viewer.

According to the preferred embodiment of the present invention, the predetermined working time that ranges from 45 minutes to 1 hour and the predetermined resting time that ranges from 5 to 15 minutes are saved in the timer module 5. As soon as the viewer turns on the electronic device, the timer module 5 starts counting down the predetermined working time. And when the countdown reaches zero, the timer module 5 then sends out a signal, through the control module 2, to the memory module 3, so that the memory module 3 saves all the working information, data, or files that the viewer is working on, before the system temporarily freezes the working mode and switches over to the resting mode in the rest enforcement module 4.

Once the resting mode is activated, the timer module 5 starts another new countdown for the predetermined resting time. After the predetermined resting time is over, the system then switches the electronic device from the resting mode back to the working mode and resumes all operations prior to the mandatory rest. The viewer is instructed to rest their eyes for 5 to 15 minutes after approximately every one hour of using the electronic device. The timer module 5 will repeat the countdown after switching back to the working mode, and ultimately, a loop is formed and intermittent break times are enforced.

The rest enforcement module 4 further comprises a plurality of types of display options for the resting mode, wherein these options are used to either "freeze" the current work display, or "replace" it with a totally different program designed for visual relaxation. The resting mode display can have any of the following options: a "freezing-mode" that temporarily freezes the current display of the working mode; a picture that is soothing for the eyes; a simple game designed for visual relaxation or ocular movements; an instruction for ocular exercises or an instruction for stretching exercises, and etc. . . .

The viewer database 6 comprises the storage of both the viewer information and the viewer preferences, wherein the database has a setting function with an input interface provided for the viewers to key in their personal information such as name, age, and select their preferences of desired working time, resting time, and activities performed during the resting mode. This customization substantially helps the system in choosing the appropriate games or pictures for the age group during the resting mode of the resting enforcement module 4. In other words, the viewer database 6 of the system is provided so that program can accommodate multiple users (viewers) for that particular electronic device 1. When the electronic device 1 is turned on, the vision protection system of the present invention is programmed to ask the viewer to select his/her name from the list of viewers already saved, so that system can upload that user's setting accordingly before the normal operation of the electronic device can begin.

It is worth mentioning that the timer module 5 automatically starts counting down the predetermined working time when the electronic device is turned on. The viewer can install the vision protection system to the electronic device 1, so that when the viewer turns on the electronic device 1, the timer module 5 automatically starts counting down the predetermined working time so as to activate the vision protecting system.

The vision protection system further comprises a detecting device 7, provided to measure the working distance between the viewer and the display of the electronic device 1, wherein when the electronic device 1 is turned on, the control module 2 activates the detecting device 7 simultaneously to determine the proper working distance. The detecting device 7 can be embodied to use a sensor such as infrared, radio wave, laser, sonar, microwave, optical sensor, optical range sensor, radar, or other alternatives to detect the working distance. The detecting device 7 may be built in or mounted on the display of the electronic device 1 and faces toward the viewer, so that if the distance measured by the detecting device 7 between the viewer and the display of the electronic device 1 falls below a predetermined range, the system will generate a warning message or signal on the screen to instruct the viewer to move back to maintain the proper working distance between the display and the viewer. Moreover, if the viewer continues to ignore this message for more than a predetermined warning time, the system will temporarily freeze the electronic device 1, and immediately switch to the resting mode before it can resume operation.

In other words, after activation of the system of the present invention, the step of gathering viewer information and the step of detecting the working distance start simultaneously. Take a 17" display of a computer screen for example, after activating the working-distance detector 7, it will monitor the actual working distance continuously to make sure that the proper distance is kept at all times. When the working distance falls below for example 45 cm, the system will generate a warning message on the display to advice the viewer to move back. If the viewer continues to ignore that message for more than 10 seconds, for example, the system will temporarily freeze the electronic device immediately for 5 minutes before it can resume operation.

The vision protection system can further be enhanced with the service and support of an eye doctor, wherein the doctor will be assigned a personal ID number, so that if the program/system is purchased directly from the viewer's eye doctor, he or she can enter that ID number during the initial set-up. In that way, a manager of the system can track and pay out the commission to the doctor accordingly, and approximately 30 days before the system expires, a reminding message will appear on the display of the electronic device every time it's turned on, not only to tell the viewer that it's time to renew the system, but also it's time to get his/her eyes examined, with the doctor's contacting information attached next to it.

As mentioned above, the vision protection system can be bypassed with a preset password that can be entered by people such as parents for emergency reasons. For example, if a child needs to finish his/her homework and it is getting really late at night, the parent can simply choose to bypass the system by entering the password. Another example will be two people taking turns using the electronic device. The viewers can bypass the resting mode with the password, so that they can skip the unnecessary resting time.

It is also important to mention that the eyesight/vision protection system will have a default setting for rest enforcement module 4, timer module 5, and detecting device 7. These default settings are designed as the safety net in cases where viewers fail to set up the program/system properly or if they are uncertain about the ideal working time, resting time, or working distance for them.

Figure 3:
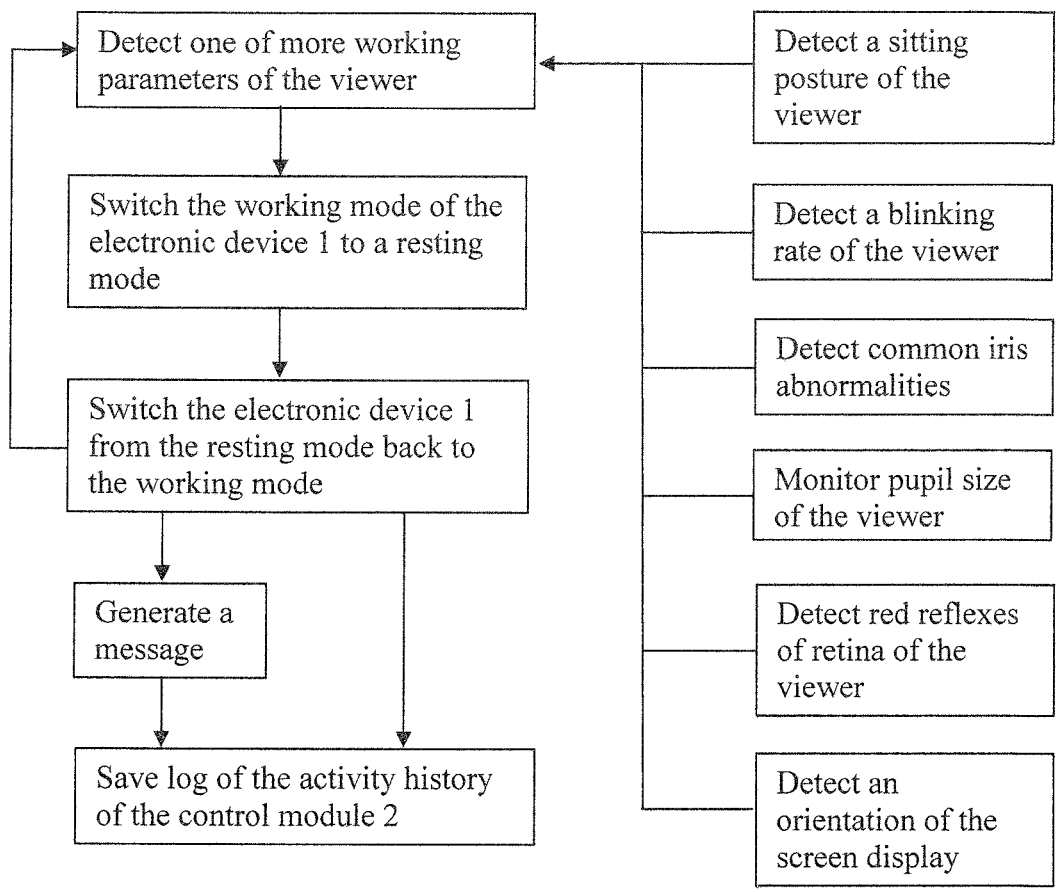
FIG. 3 is a flow chart of a method for protecting the eyesight of an electronic device viewer according to the preferred embodiment of the present invention, illustrating a modification of the method.
Figure 4:
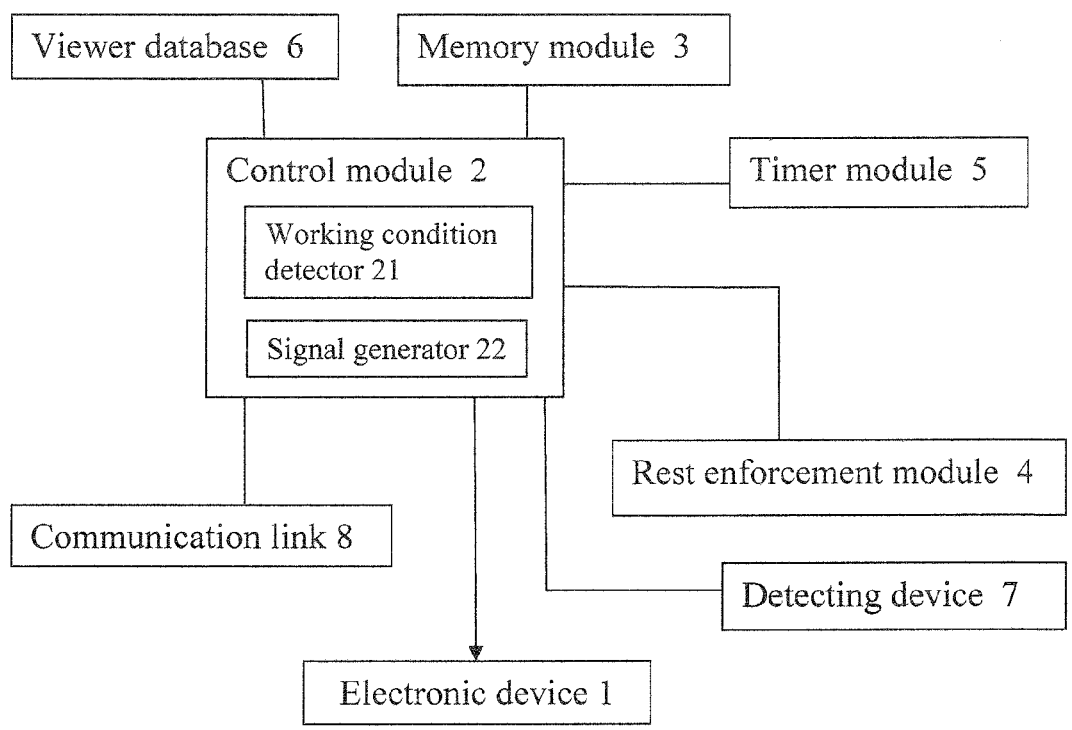
FIG. 4 is a block diagram of the modified vision protection system according to the preferred embodiment of the present invention.

As shown in FIG. 3, the present invention further provides a modification of a method for eyesight protection of an electronic device viewer, which comprises the following steps.

(1) Detect one of more working parameters of the viewer in responsive to a preset working threshold in a working mode of the electronic device 1 during the viewer is working on a current work displaying by the electronic device 1.

(2) Switch the working mode of the electronic device 1 to a resting mode when the working parameter is over the working threshold for protecting the viewer from excessive usage of the electronic device 1 by halting a screen display of the current work so as to ensure the viewer to rest eyes thereof for a predetermined resting time.

(3) Switch the electronic device 1 from the resting mode back to the working mode to resume the display of the current work of the electronic device 1 after the predetermined resting time has elapsed.

(4) Repeat the above steps (1) to (3) to form a loop continuously until the viewer terminates operating the electronic device 1 so as to ensure the viewer opportunities to have intermittent rests of eyes thereof after each of the predetermined working times.

As it is mentioned above, the vision protection method of the present invention can be embodied to be performed by a system equipped with the electronic device 1. The vision protection system for the viewer of the electronic device 1 comprises a control module 2 for coordinating the devices or modules, a memory module 3 for saving the working information, data, or files that the viewer is currently working on, a rest mode enforcement module 4 where a plurality of resting mode activities are stored, a timer module 5 that does the countdown for both the predetermined working time and resting time, and a viewer database 6 for saving the information and preference of the viewer.

The control module 2 has a preset working threshold and comprises a working condition detector 21 for detecting one of more working parameters of the viewer in a working mode of the electronic device 1 during the viewer is working on a current work displaying by the electronic device 1. Accordingly, the working condition detector 21 can be the detecting device 7 as mentioned above to measure the working distance between the viewer and the display of the electronic device 1.

In addition, the control module 2 further comprises a signal generator 22 operatively linked to the rest mode enforcement module 4 for generating a message on the screen display when the electronic device 1 is switched to the resting mode.

In this modification, the working condition detector 21 comprises an image capturer operatively linked to the rest mode enforcement module 4 for detecting a working condition of the viewer including sitting posture of the viewer, blinking rate of the viewer, common iris abnormalities, pupil size of the viewer, red reflexes of retina of the viewer, and orientation of the screen display. In particular, the image capturer of the working condition detector 21 comprises a high-resolution camera with facial recognition module adapted for being installed into the electronic device 1 for detecting the working condition of the viewer. The high-resolution camera can be mounted onto the screen display or built-in with the screen display for capturing an image of the viewer in front of the screen display. The facial recognition module can be embodied as a software being installed into the electronic device 1 in order to operatively link with the high-resolution camera.

In the step (1), the working condition detector 21 is arranged for detecting a sitting posture of the viewer as one of the working parameters of the viewer, wherein when an improper sitting height of the viewer is detected, the electronic device 1 is switched from the working mode to the resting mode. Accordingly, the working condition detector 21 will monitor the sitting position of the viewer that if improper sitting height is detected, correction will be required to ensure proper usage of the screen display. In this situation, the signal generator 22 will generate a sitting posture message on the screen display for notifying the viewer to correct the sitting posture.

The working condition detector 21 is also arranged for monitoring a blinking rate of the viewer as one of the working parameters of the viewer. Accordingly, when the blinking rate of the viewer is below the working threshold, the electronic device 1 is switched from the working mode to the resting mode. Since the blinking rate decreases as the eyes are fixating on an object, such as the screen display, it is a major cause of electronic device-related dry eye problems. The control module 2 will count each blink and if the rate fails dangerously low, the signal generator 22 will provide a warning message.

The working condition detector 21 is also arranged for capturing the common iris abnormalities as one of the working parameters of the viewer, wherein when the common iris abnormalities is detected, the signal generator 22 will generate an advising message on the screen display for advise the viewer to seek professional opinion.

The working condition detector 21 is also arranged for monitoring the pupil size of the viewer to prevent pseudo-myopia. Accordingly, the viewers, especially for younger users, can over-use the electronic device causing their tiny eye muscles (called ciliary muscles) to stain. Hence, the size of the pupil will be more constricted than usual. By detecting the unusually small pupil size of the younger users, the control module 2 can adjust the resting time accordingly.

The working condition detector 21 is also arranged for detecting the red reflexes of the healthy retina in kids. Retinoblastoma is one of the most serious causes for childhood blindness. People who suffer from it will lose the red reflexes from the retina when a light source is shined into the eyes. The camera of the working condition detector 21 with a light source will capture a baseline photo and the control module 2 will then analyze the reflexes. If unusual reflexes are found, the signal generator 22 will generate an advising message on the screen display that guardian or parents will be notified.

The working condition detector 21 further comprises an orientation monitor operated coupled with the screen display, wherein the orientation monitor can be a gyroscope or an oscillation monitor to ensure the viewer of the electronic device 1 is not lying down or use the device in a moving vehicle when excessive movement can potentially strain the eyes even further.

As it is mentioned above, during the resting mode, the rest mode enforcement module 4 will selectively provide one or more of the resting mode activities including:

(i) idling the electronic device 1 for the predetermined resting time, (ii) temporarily freezing the current work of the electronic device 1, (iii) temporarily blanking out the screen display of the electronic device 1 for the predetermined resting time so as to stop the viewer from viewing the display of the electronic device, (iv) replacing the screen display of the current work of the electronic device 1 with a graphic display that is soothing for the eyes of the viewer for the predetermined resting time, (v) playing relaxing audio sounds, and (vi) running a program selected from a group consisting of a visual therapy game for relaxing muscles of the eyes of the viewer, a game for eye movement exercises, and an instruction for stretching exercises. Accordingly, an iridology program will be provided for entertainment purposes.

It is worth mentioning that the resting mode activities can be pre-selected by the viewer or can be preset by the rest mode enforcement module 4 that one of the resting mode activities will be randomly activated. In addition, the current working information and data of the working mode will be automatically saved when the electronic device 1 is switched at the resting mode. Once the electronic device 1 is activated to return back to the working mode, the electronic device 1 resumes all the current working information and data and the viewer is able to continue from where the viewer was left off right before the resting mode is re-activated.

The system of the present invention may further comprises a communication link 8 operatively linked to the control module 2, wherein the control module 2 can be remotely controlled through the communication link 8. Therefore, the parents can monitor and supervise the kid as the viewer in a distance. Accordingly, the communication link 8 is preferably an Internet connection link or a phone line connection link that the signal generator 22 can link to the mobile phone of the parents through the communication link 8, such that the signal generator 22 not only generates the message on the screen display of the electronic device 1 when the electronic device 1 is switched at the resting mode, but also generates a message such as a text message to the mobile phone of the parents through the communication link 8.

In addition, the viewer database 6 can be linked to the database of the eye doctor through the communication link 8, such that the eye doctor can instantly notify any eye problem of the viewer, especially the common iris abnormalities and/or symptom of Retinoblastoma being detected by the working condition detector 21. Accordingly, the log of the activity history of the control module 2 will be saved in the viewer database 6 for analysis purpose.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A vision protection method for eyesight protection of a viewer of an electronic device viewer, comprising the steps of:
(a) detecting one of more working parameters of the viewer in responsive to a preset working threshold in a working mode of the electronic device during the viewer is working on a current work displaying by the electronic device, wherein one of said working parameters is selected from a group of steps consisting of:
detecting a sitting posture of the viewer, wherein when an improper sitting height of the viewer is detected, the electronic device is switched from the working mode to the resting mode;
detecting a blinking rate of the viewer, wherein when the blinking rate of the viewer is below the working threshold, the electronic device is switched from the working mode to the resting mode;
detecting common iris abnormalities, wherein when the common iris abnormalities is detected, an advising message is generated on the screen display for advise the viewer to seek professional opinion;
monitoring pupil size of the viewer to prevent pseudomyopia;
detecting red reflexes of retina of the viewer; and
detecting an orientation of the screen display;
(b) switching the working mode of the electronic device to a resting mode when the working parameter is over the working threshold for protecting the viewer from excessive usage of the electronic device by halting a screen display of the current work so as to ensure the viewer to rest eyes thereof for a predetermined resting time;
(c) switching the electronic device from the resting mode back to the working mode to resume the display of the current work of the electronic device after the predetermined resting time has elapsed; and
(d) repeating the above steps (a) to (c) to form a loop continuously until the viewer terminates operating the electronic device so as to ensure the viewer opportunities to have intermittent rests of eyes thereof after each of the predetermined working times.

2. The method, as recited in claim 1, wherein, during the resting mode in the step (b), the electronic device generates a sitting posture message on the screen display for notifying the viewer to correct the sitting posture.

3. The method, as recited in claim 2, wherein, during the resting mode in the step (b), the electronic device temporarily freezes the current work.

4. The method, as recited in claim 3, wherein during the resting mode, the resting mode activities are selected from a group consisting of:
(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

5. The method, as recited in claim 2, wherein during the resting mode, the resting mode activities are selected from a group consisting of:
(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

6. The method, as recited in claim 1, wherein, during the resting mode in the step (b), the electronic device temporarily freezes the current work.

7. The method, as recited in claim 6, wherein during the resting mode, the resting mode activities are selected from a group consisting of:
(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

8. The method, as recited in claim 1, wherein during the resting mode, the resting mode activities are selected from a group consisting of:
(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

9. A vision protection system for eyesight protection of a Viewer of an electronic device, comprising:

a control module for coordinating and communicating with the electronic device, wherein said control module has a preset working threshold and comprises a working condition detector for detecting one of more working con of the viewer in a working mode of the electronic device during the viewer is working on a current work displaying by the electronic device, wherein one of said working parameter is selected from a group consisting of:

a sitting posture of the viewer, wherein when an improper sitting height of the viewer is detected, the electronic device is switched from the working mode to the resting mode;

a blinking rate of the viewer, wherein when the blinking rate of the viewer is below the working threshold, the electronic device is switched from the working mode to the resting mode;

common iris abnormalities, wherein when the common iris abnormalities is detected, an advising message is generated on the screen display for advise the viewer to seek professional opinion;

pupil size of the viewer to prevent pseudomyopia;

red reflexes of retina of the viewer; and an orientation of the screen display; and a rest mode enforcement module having one or more resting mode activities for switching said working mode of the electronic device during which the viewer is working on the current work displaying by the electronic device to a resting mode during which one of the resting mode activities substitutes the current work for protecting the viewer from excessive usage of the electronic device by halting a screen display of the current work thereof so as to ensure the viewer to rest eyes thereof.

10. The system, as recited in claim 9, wherein said working condition detector comprises an image capturer operatively linked to said rest mode enforcement module for detecting said one of more working parameter.

11. The system, as recited in claim 10, wherein said image capturer comprises a high-resolution camera with facial recognition module adapted for being installed into the electronic device for detecting the working condition of the viewer.

12. The system, as recited in claim 11, wherein said control module further comprises a signal generator operatively linked to said rest mode enforcement module for generating a message on the screen display when the electronic device is switched to the resting mode.

13. The system, as recited in claim 12, further comprising a timer module, after the system is activated, counting down a predetermined working time in the working mode and a predetermined resting time of the resting mode of the electronic device, wherein when the timer module counts down until the predetermined working time expires, the working mode of the electronic device is switched to the resting mode of the rest enforcement module through the control module, and that when the timer module counts down until the predetermined resting time expires, the electronic device is switched back from the resting mode to the working mode to resume the current work of the electronic device so that a loop is formed until the viewer deactivates the system so as to ensure the viewer opportunities to have intermittent rests of the eyes thereof after each of the predetermined working times.

14. The system, as recited in claim 13, wherein during the resting mode, the resting mode activities are selected from a group consisting of:

(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

15. The system, as recited in claim 12, wherein during the resting mode, the resting mode activities are selected from a group consisting of:

(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

16. The system, as recited in claim 11, wherein during the resting mode, the resting mode activities are selected from a group consisting of:

(i) idling the electronic device for the predetermined resting time,
(ii) temporarily freezing the current work of the electronic device,
(iii) temporarily blanking out the screen display of the electronic device for the predetermined resting time so as to stop the viewer from viewing the display of the electronic device,
(iv) replacing the screen display of the current work of the electronic device with a graphic display that is soothing for the eyes of the viewer for the predetermined resting time,
(v) playing relaxing audio sounds, and
(vi) running a program selected from a group consisting of a visual therapy game for relaxing muscles of the eyes of the viewer, a game for eye movement exercises, and an instruction for stretching exercises.

17. The system, as recited in claim 10, wherein said control module further comprises a signal generator operatively linked to said rest mode enforcement module for generating a message on the screen display when the electronic device is switched to the resting mode.

18. The system, as recited in claim 17, wherein during the resting mode, the resting mode activities are selected from a group consisting of:

(i) idling the electronic device for the predetermined resting time, (ii) temporarily freezing the current work of the electronic device, (iii) temporarily blanking out the screen display of the electronic device for the predetermined resting time so as to stop the viewer from viewing the display of the electronic device, (iv) replacing the screen display of the current work of the electronic device with a graphic display that is soothing for the eyes of the viewer for the predetermined resting time, (v) playing relaxing audio sounds, and (vi) running a program selected from a group consisting of a visual therapy game for relaxing muscles of the eyes of the viewer, a game for eye movement exercises, and an instruction for stretching exercises.

19. The system, as recited in claim 10, wherein during the resting mode, the resting mode activities are selected from a group consisting of:

(i) idling the electronic device for the predetermined resting time, (ii) temporarily freezing the current work of the electronic device, (iii) temporarily blanking out the screen display of the electronic device for the predetermined resting time so as to stop the viewer from viewing the display of the electronic device, (iv) replacing the screen display of the current work of the electronic device with a graphic display that is soothing for the eyes of the viewer for the predetermined resting time, (v) playing relaxing audio sounds, and (vi) running a program selected from a group consisting of a visual therapy game for relaxing muscles of the eyes of the viewer, a game for eye movement exercises, and an instruction for stretching exercises.

20. The system, as recited in claim 9, wherein during the resting mode, the resting mode activities are selected from a group consisting of:

(i) idling the electronic device for the predetermined resting time, (ii) temporarily freezing the current work of the electronic device, (iii) temporarily blanking out the screen display of the electronic device for the predetermined resting time so as to stop the viewer from viewing the display of the electronic device, (iv) replacing the screen display of the current work of the electronic device with a graphic display that is soothing for the eyes of the viewer for the predetermined resting time, (v) playing relaxing audio sounds, and (vi) running a program selected from a group consisting of a visual therapy game for relaxing muscles of the eyes of the viewer, a game for eye movement exercises, and an instruction for stretching exercises.

* * * * *